US 6,669,643 B1

(12) United States Patent
Dubinsky

(10) Patent No.: US 6,669,643 B1
(45) Date of Patent: Dec. 30, 2003

(54) METHOD AND APPARATUS FOR SONOGRAPHIC EXAMINATION, BIOPSY, AND EXCISION

(76) Inventor: Theodore J. Dubinsky, 7409 - 34th Ave. NW., Seattle, WA (US) 98117

( * ) Notice: Subject to any disclaimer, the term of this patent is extended or adjusted under 35 U.S.C. 154(b) by 0 days.

(21) Appl. No.: 09/673,332

(22) PCT Filed: Apr. 13, 1999

(86) PCT No.: PCT/US99/08011

§ 371 (c)(1),
(2), (4) Date: Oct. 13, 2000

(87) PCT Pub. No.: WO99/52441

PCT Pub. Date: Oct. 21, 1999

Related U.S. Application Data

(60) Provisional application No. 60/081,650, filed on Apr. 13, 1998.

(51) Int. Cl.[7] .................................................. A61B 8/14
(52) U.S. Cl. ........................ 600/459; 600/461; 600/463; 600/464
(58) Field of Search ...................... 600/407–471; 604/116, 164, 280; 601/2, 3; 607/122; 73/625, 626

(56) References Cited

U.S. PATENT DOCUMENTS

| | | | |
|---|---|---|---|
| 4,576,175 A | 3/1986 | Epstein | 128/660 |
| 4,742,829 A * | 5/1988 | Law et al. | 600/461 |
| 4,802,487 A | 2/1989 | Martin et al. | 128/662.06 |
| 4,819,650 A * | 4/1989 | Goldstein | 600/447 |
| 4,877,033 A * | 10/1989 | Seitz, Jr. | 600/441 |
| 5,076,279 A | 12/1991 | Arenson et al. | 128/662.05 |
| 5,090,414 A * | 2/1992 | Takano | 600/461 |
| 5,147,335 A | 9/1992 | Wright | 604/280 |
| 5,178,150 A | 1/1993 | Silverstein et al. | 128/662.06 |
| 5,199,437 A * | 4/1993 | Langberg | 600/463 |
| 5,383,465 A | 1/1995 | Lesny et al. | 128/662.05 |
| 5,398,690 A | 3/1995 | Batten et al. | 128/662.05 |
| 5,456,259 A | 10/1995 | Barlow et al. | 128/662.03 |
| 5,513,639 A | 5/1996 | Satomi et al. | 128/660.1 |
| 5,596,991 A | 1/1997 | Tanaka | 128/662.06 |
| 5,599,300 A | 2/1997 | Weaver et al. | 604/54 |
| 5,606,974 A | 3/1997 | Castellano et al. | 128/662.06 |
| 5,651,364 A | 7/1997 | Yock | 128/660.03 |
| 5,833,611 A * | 11/1998 | Tepper et al. | 600/462 |

* cited by examiner

Primary Examiner—Ali M. Imam
(74) Attorney, Agent, or Firm—David L. Garrison; Garrison & Assoc. PS

(57) ABSTRACT

Method and apparatus for internal examination of human and other subjects employing special catheters and biopsy wires, in combination with sonographic or fluoroscopic transducers, to provide unprecedented accuracy, economy, and efficiency in internal examination, diagnosis, biopsy, and surgical removal of lesions, tumors, polyps, etc. from bodies. In one aspect the invention provides an apparatus for use in combination with a sonographic transducer for examination and performing biopsies within a vaginal and uterine chamber of a human female and other bodies, whereby the apparatus is comprised of a substantially tubular catheter and any of a wide variety of biopsy devices adapted for disposition on or within the catheter. In another aspect, the invention provides a method of using sonographic or fluoroscopic imaging in combination with the apparatus to examine the cavities under study and to guide the apparatus during a biopsy procedure.

22 Claims, 6 Drawing Sheets

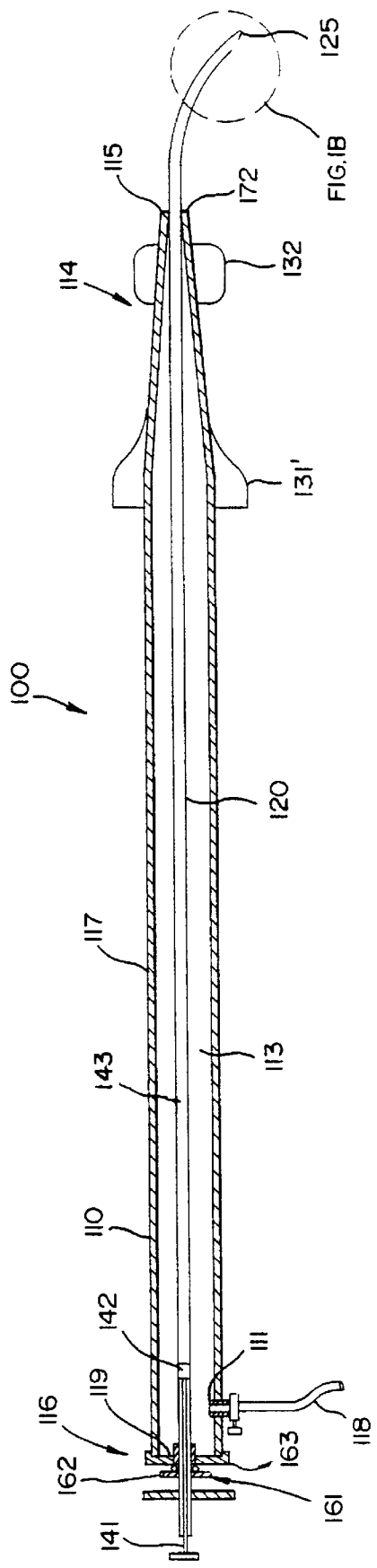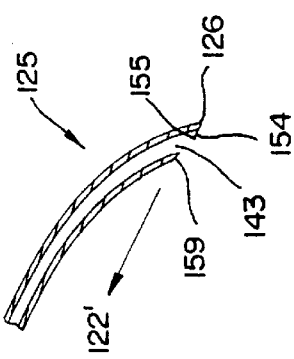
FIG. 1A
FIG. 1B

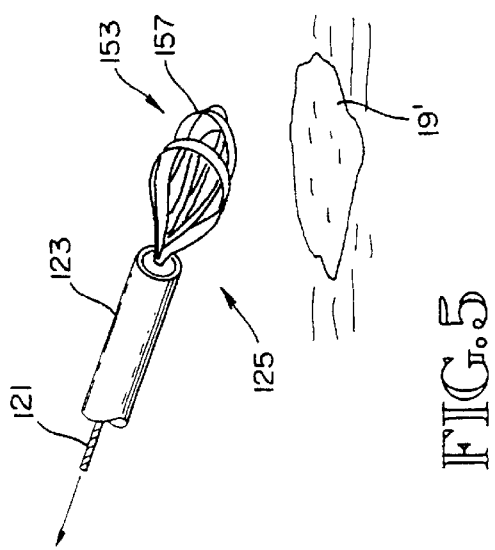
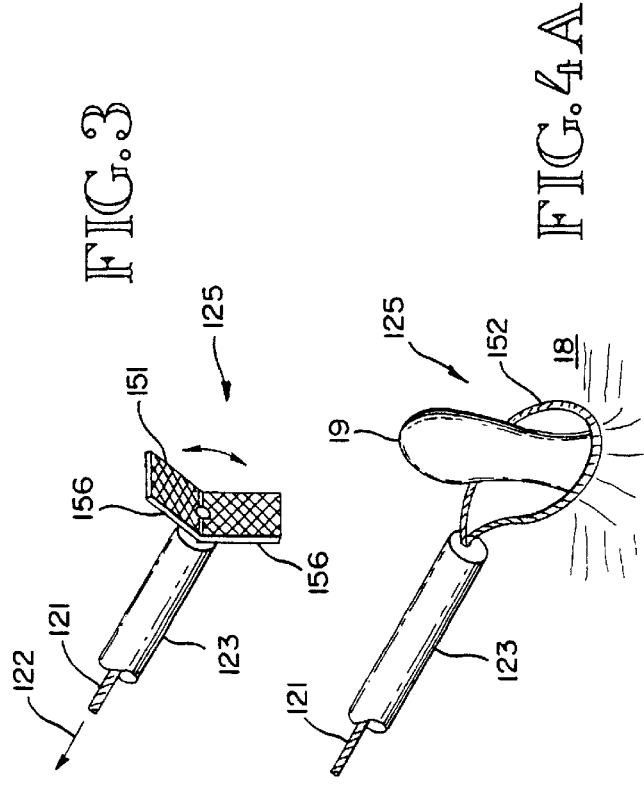
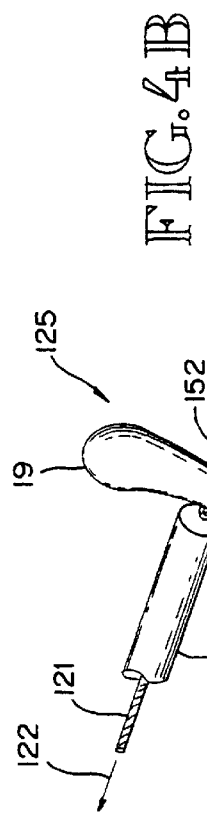

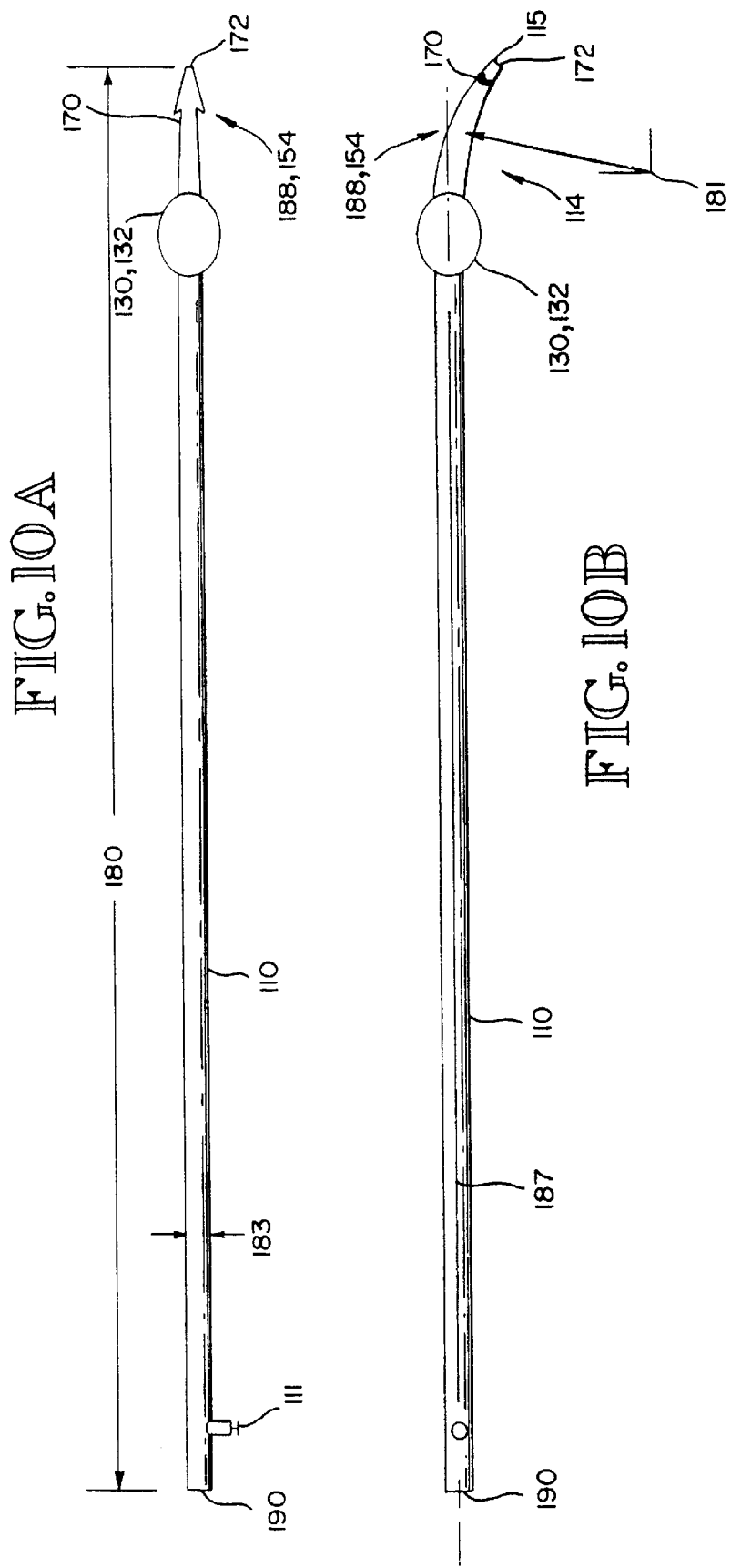

METHOD AND APPARATUS FOR SONOGRAPHIC EXAMINATION, BIOPSY, AND EXCISION

This application claims the benefit of United States provisional patent application Ser. No. 60/081,650, entitled Method and Apparatus for Sonographic Examination, Biopsy, and Excision, filed Apr. 13, 1998.

TECHNICAL FIELD

The invention relates to method and apparatus for sonographic or fluoroscopic examination, biopsy, and excision; more particularly, it relates to method and apparatus for sonographic examination, biopsy, and excision within multichambered cavities of human and other bodies.

BACKGROUND OF THE INVENTION

It is well established that the examination of body cavities is an important part of human and animal health care. Through examination of the interior of body cavities a wide variety of undesirable health conditions may be diagnosed and treated. For example, the examination of the interior of human and animal mouths for rotting and other conditions in teeth has long been practiced. A more difficult proposition, however, has been the examination of more remote or obstructed body cavities. For example, it has only recently become possible to examine the uterus of a human female without cutting the woman open and removing it. Moreover, a survey of the state of the art reveals that there is room for much improvement in the examination and treatment of body cavities, including the retrieval of biopsy samples.

An excellent example of the need for improvement in procedures and apparatus for the examination of interior body cavities is the current state of the art in uterine examination and biopsy. It has been shown that peri-and post-menopausal vaginal bleeding (PMB) is one of the most frequent reasons for postmenopausal women to seek medical attention. In the United States, such bleeding accounts for approximately 5% of all gynecologic visits; and conservative estimates predict that over the next ten years at least one million women a year within the U.S. will develop PMB. Historically, women found to suffer from PMB were subjected to hysterectomies: the complete surgical removal of the uterus. As in the case of any major surgery, however, hysterectomy has associated risks. Yet at one time hysterectomy was the most commonly performed surgical procedure in the United States.

A recent proposal as a substitute for the performance of hysterectomies has been hormone replacement therapy. Hormone replacement therapy has met with success in approximately 80% of premenopausal and approximately 50% of postmenopausal women suffering from PMB. But it has been found that hormone replacement therapy increases the risk of endometrial and breast carcinoma. Moreover, like surgical removal of suspected and (arguably) unneeded organs, hormone replacement therapy fails to treat all causes of bleeding, such as fibroid conditions, polyps, hyperplasia, and carcinoma. Thus, while hormone replacement therapy has gained widespread acceptance, it will not benefit all women.

Other proposals for the treatment of PMB and like conditions in body cavities difficult to access have included dilation and curettage procedures, and blind aspiration biopsy. Dilation and curettage comprises dilation of the cervix while the patient is under at least a local anesthesia, and the scraping of the endometrium with a spoon-like probe. Anaesthesia having been shown to be generally undesirable where not strictly necessary, however, blind aspiration biopsy techniques not generally requiring anaesthesia have been developed. But blind procedures are limited in usefulness due to low sensitivity. Blind procedures are termed "blind" because they involve the unguided recovery of samples taken at random from what can at most amount to a limited region of the cavity, using equipment such as suction aspiration devices or curettage instruments inserted into various body cavities without benefit or capability of visual, sonic, or other guidance. Thus the removal of samples by blind procedures gives a fair indication of the presence or absence of a malignancy with only about a 60% to 80% sensitivity. However, most recent studies have shown very low prevalences for endometrial carcinoma. Not infrequently a sample of healthy tissue is removed from the wall of a cavity within very close proximity to an undiscovered, and therefore untimely treated, malignancy.

The emerging standard of care in health care is to look at, or monitor, what is being sampled or diagnosed. Accordingly, at least one proposed alternative to the foregoing procedures has employed fiber optic spectroscopy equipment to guide the removal of tissue samples. But fiber optic equipment has been found to be, for many applications—for example, uterine examination—too large to be used without patient discomfort, and its use has therefore often required the use of anaesthetics. Moreover, fiber optic equipment, due to functionally-dictated design shapes, is prone to cause injury to sensitive internal tissues and also to missing even previously located malignancies, and is difficult to guide to ensure examination of the entire cavity. Furthermore, fiber optic procedures are expensive: the average current cost for performing a fiber optic examination is about $1800.

In addition, much key information which may be gleaned from the thickness, homogeneity, and displacement of some internal tissue structures, as for example the endometrium, is unavailable through either biopsy or fiber optic procedures because neither blind biopsy needles nor fiber optic devices are capable of reliably determining internal strictural shapes or sizes, or of determining tissue thicknesses.

Moreover, many of the above-described treatments are in-patient procedures, involving hospital stays of at least one night, second and sometimes subsequent return visits, and often substantial discomfort to the patient. The treatments also frequently result in at least temporary or partial incapacitation of the recipient, including (in uterine examinations) the ability to engage in sexual intercourse.

Perhaps the most troubling difficulty with prior art procedures for the treatment of PMB, however, has been that they are conducted based on the assumption that there exists within the patient a malignancy to be found: it has in fact been found that most women who suffer from PMB bleed for other reasons. The performance of procedures like those discussed above, therefore, can result in needless discomfort, including possible injury or infection to the patient, and in substantial economic and material waste as well.

Progress has been made through the employment of ultrasonic or sonographic or fluorographic equipment. Sonographic equipment is capable of mapping interior surfaces of cavities and tissue structures without unduly invasive or incisive intrusion, and generally without the necessity of piercing or cutting the patient. Moreover, sonographic equipment can survey the thickness and echogenicity of tissue structures such as the endometrium. But none of the sonographic attempts made so far have provided safe, economic, efficient, or accurate means for examining and removing biopsy samples and malignancies from the interior of body cavities, and especially multichambered cavities such as the human vagina and uterus.

Devices are known which combine biopsy devices with ultrasonic probes. Such combinations are shown in U.S. Pat. No. 4,576,175 to Epstein; U.S. Pat. No. 5,076,279 to Arenson et al; U.S. Pat. No. 5,398,690 to Batten et al.; and 5,596,991 to Tanaka. The devices taught by these references, however, each comprise a biopsy device integrally (and in most cases rigidly, i.e. non-rotatably) attached to a sonographic transducer. In the cases of Epstein, Arenson, and Tanaka, the biopsy devices are immovably attached to the transducer heads, while Batten allows some rotation of the biopsy device. But such devices are not satisfactory for use within the often curved, typically restricted spaces of multichambered cavities such as the uterus and vagina. The sheer bulk of the equipment precludes its use in many restricted cavities. Moreover, such apparatus is frequently unsatisfactory for use inside the body because the needle and transducer cannot be independently manipulated—either at all, or (as in the case of the Batten device) to any adequate extent: the biopsy device being fixed to the transducer head, the needle and head must be manipulated together. Thus for example if a sweep survey of a cavity were attempted with such devices the biopsy needle would have to be swept back and forth with the transducer head, resulting at least in restriction of the movement of the transducer head, with consequent loss in the quality of the sonic survey, and not improbably in injury to the patient. Another effect is that because the biopsy device is fixed to the transducer head, it is impossible to gain as wide a view of the interior of the examined cavity while guiding the biopsy device as is possible (as taught herein) with separate devices. It is impossible, for example, with fixed devices to back the transducer head away from the biopsy needle or the inner portions of the cavity(ies) in general so as to broaden the perspective seen via the transducer without withdrawing the biopsy device.

Nor do devices like those taught in Epstein and Arenson allow for removal of the biopsy needle (with or without sample), and replacement of the needle with another device such as a snare adapted for the removal of polyps, without requiring removal of the entire transducer head and the necessity of starting the entire procedure again. Thus flexibility in examination, biopsy, and excision using devices of the type disclosed in the cited specifications is extremely limited.

U.S. Pat. No. 5,383,465 to Lesny et al. discloses a high-frequency ultrasonic instrument, also rigidly fixed to a biopsy probe. In addition to the limitations suffered by the fixed devices described above, the Lesny device is incapable of performing a broad-perspective examination of an interior organ under any circumstances. The types of transducers disclosed in Lesny permit only a very small (on the order of 16 millimeters diameter) viewing area. Thus devices of the Lesny type are capable (especially when rigidly wedded to a biopsy device) of examining only a limited portion of a cavity, and must be guided into position by other means, such as a fluoroscope.

U.S. Pat. No. 5,651,364 to Yock discloses method and apparatus for intravascular ultrasonic imaging and atherectomy. The apparatus comprises an ultrasound transducer disposed within a catheter, with capacity for carrying an atherectomy device or other rotary cutter and a balloon for urging the atherectomy device toward an atheroma for removal. In addition to suffering the sanie limitations described above for the other prior-art devices, including the Lesney device, the Yock apparatus comprises no means for removing a biopsy sample; it is adapted only for the loosening of unwanted material within blood vessels into the blood stream and is entirely unsuited to the performance of examination, biopsies, and excision within cavities of the type contemplated herein. Also, placement of the device must be performed under fluoroscopic guidance rather than ultrasound. Fluoroscopy exposes the patient to radiation, and virtually necessitates that the procedure be performed in a fluoroscopy suite, whereas ultrasound machines are portable, and ultrasound guided procedures can be performed anywhere, including at a patient's hospital bedside. Moreover, like the other references, the Yock device is needlessly complex and expensive, both to make and operate, for the purposes disclosed herein.

Thus there is a need for a procedure for examining the interior of multi-chambered or curved, restricted-access cavities within human and other bodies, and for guiding biopsy or excision equipment to the location of lesions or other undesirable tissues or growths within the cavities, and of conducting the excision and removal of biopsy samples or undesirable tissues or growths in a simple, cost effective, reliable, and accurate manner, at reduced risk to the patient and without unnecessary agitation or removal of tissue—particularly healthy tissue. It is especially desirable that such procedures be accomplished without the necessity of removing or exchanging equipment already in place and in contact with the cavity or body, and especially equipment which is in contact with the walls of the cavity itself. There is a further need for apparatus with which to accomplish these ends.

DISCLOSURE OF THE INVENTION

Accordingly, it is an object of the invention to provide a simple, cost effective, reliable, and accurate procedure for examining the interior of multi-chambered or curved, restricted-access cavities within human and other bodies, and for guiding biopsy or excision equipment to the location of lesions or other undesirable tissues or growths within the cavity, and of conducting the excision and removal of biopsy samples or undesirable tissues or growths in a simple, cost effective, reliable, and accurate manner, without the removal or agitation of healthy or otherwise desired tissue.

It is a further object of the invention to provide procedures which permit the realization of the foregoing objects without the necessity of removing, disturbing, or exchanging equipment, and especially guidance equipment positioned within the body, and particularly within the walls of the cavity itself, while the procedure is being conducted.

It is a further object of the invention to provide procedures to accomplish the foregoing with reduced risk and reduced or no requirements for hospital stays.

It is a further object of the invention to provide apparatus with which to accomplish those ends.

It is yet another object of the invention to meet any or all of the needs summarized above.

These and such other objects of the invention as will become evident from the disclosure below are met by the invention disclosed herein. The invention is method and apparatus for internal examination of human and other subjects employing specially-modified catheters and biopsy wires, in combination with sonographic transducers, to provide unprecedented accuracy, economy, and efficiency in internal examination, diagnosis, biopsy, and surgical removal of lesions, tumors, polyps, etc.

In one aspect the invention provides apparatus for use, in combination with sonographic or fluoroscopic transducers, in the examination of and performance of biopsies within externally communicating multi-chambered body cavities comprising communicating inner and outer chambers, or within the curved or restricted spaces of externally communicating single-chamber cavities. In general the apparatus comprises a substantially tubular catheter adapted for insertion within a cavity, or into a multi-chambered cavity at least as far as the outer chamber; and a any of a wide variety of biopsy devices adapted for disposition on or within the catheter, and for deeper insertion into the cavity, or for insertion into the inner chamber through the catheter. By such means, and upon sonographic or fluoroscopic examination of the cavity, or of the inner chamber, abnormalities within the cavity may be located and the biopsy device may be guided to an abnormality, and the biopsy device may be used to remove from the inner chamber a sample of the abnormality. In cases in which the apparatus is used to examine and/or treat a multi-chambered cavity, the apparatus generally further comprises a sonographic or fluoroscopic transducer for placement proximate the inner chamber, preferably within the outer chamber, for sonographic or fluoroscopic examination of the inner chamber.

A preferred catheter according to this aspect of the invention comprises a substantially tubular body having an interior, an anterior end, and a fluid infusion port; the interior of the catheter being adapted for the accommodation of a biopsy device comprising an excision device and for the passage of a fluid, such as for example an intraluminal fluid, admitted via the fluid infusion port and delivered to the cavity in order to facilitate sonographic examination of the cavity; the anterior end of the catheter being adapted for passage and accommodation of the biopsy device and for passage of a fluid; and the fluid infusion port adapted for accommodation of a fluid infusion means and for passage of a fluid to the interior of the substantially tubular body. Such embodiments optionally comprise posterior ends adapted for fluid tight passage and accommodation of the biopsy device. Preferred catheters further comprise an offset insertion tip, to facilitate manipulation and operation of the biopsy device within the cavity, especially in the inner recesses where curved cavity walls or restricted spaces are involved. They also comprise fenders adapted to support the catheter in a selected juxtaposition relative to the cavity. In particular, such embodiments comprise either a bumper adapted to support the catheter against a wall of the cavity and thereby to restrain the catheter from insertion beyond a desired depth within the cavity, or a balloon adapted to prevent contact between a side of the catheter and a wall of the cavity, or both. It has been found advantageous in many applications to provide not one but at least two coaxially-disposed catheters, one being located inside the other, with a biopsy device being disposed in the manner previously described within the inner catheter. Optionally, catheters useful in practicing the invention, and particularly inner catheters or sheaths in those embodiments of the invention comprising more than one catheter, comprise blades adapted for the engagement and removal of tissue (such as for example polyps or samples of lesions or other malignancies), either by aspiration or by retaining the sample, as in a cusp, while the catheter is withdrawn from the subject. Preferably, such blades are reverse bias blades.

Catheters suitable for use in accordance with the invention optionally further comprise one or more side ports, preferably located in the anterior end of the catheter at or near the tip, for manipulating biopsy and excision devices and for facilitating aspiration of tissue samples. Such catheters, whether or not they comprise side ports, are optionally curved to facilitate manipulation of biopsy or excision devices and aspiration or removal of tissue samples. Provision of curves in the anterior end of such catheters has the effect of offsetting the catheter's tip from the longitudinal axis of the catheter, which improves access by the catheter and any deployed biopsy or excision devices around corners or folds of tissue, etc. Manipulation and maneuvering of catheters and appurtenant excision or biopsy devices is also improved in some cases by making at least a portion of the catheter, and most typically the anterior end of the catheter, flexible. Similar, tapering of the anterior end or of the tip of the catheter is beneficial in many circumstances.

The apparatus aspect of the invention further generally comprises a biopsy device which comprises a sample-engaging or-excision device adapted for the engagement and ultimately the removal of tissue from the cavity, the excision device being selected from the group comprising forceps, snares, baskets, cauterizing devices, graspers, brushes, suction aspiration devices, and reverse bias blades. In general, the catheter (or catheters) and biopsy device are adapted such that the device may be manipulated or operated within the cavity, or even changed for another device or instrument, without the necessity of moving or removing the catheter(s), or disturbing its location. Once the tissue has been engaged and separated from the cavity wall, it may be removed from the cavity by any satisfactory means, including aspiration or simple removal of the biopsy device through the catheter(s) in place within the cavity.

In another aspect the invention provides a procedure for the sonographic examination of multi-chambered body cavities comprising communicating inner and outer chambers, or within curved or restricted spaces of externally communicating single-chamber cavities, and for the removal of tissue or samples from such cavities. In general, the procedure aspect of the invention comprises the steps of inserting a substantially tubular catheter into the cavity, or at least as far as the outer chamber of a multi-chambered cavity; inserting an excision device deeper into the cavity, or into the inner chamber of a multi-chambered cavity, through the catheter; disposing a sonographic transducer within the cavity, or within the outer chamber in substantial proximity to the inner chamber, so as to permit sonographic examination of the inner chamber; and sonographically examining the cavity or inner chamber. In examinations of multi-chambered cavities, as for example the human uterus and/or vagina, the outer chamber will often comprise a wall proximate the inner chamber, for example between the inner and outer chambers. It is adjacent to or near this wall that the transducer is typically placed in order to facilitate sonographic examination of the inner chamber. To say that the transducer is in substantial proximity to the inner chamber is to say that it is closely enough located and suitably disposed to permit effective sonographic examination of the interior of the chamber. In cases in which lesions or other abnormalities are detected the procedure comprises the further steps of sonographically locating/identifying the abnormality(ies) within the cavity or inner chamber, guiding the biopsy device to the abnormality, and removing a sample of the abnormality by means of the excision device. This can include removing a biopsy sample(s) by means of the forceps discussed above, or cutting and removing polyps with a snare, or with suction aspirator with either a cutting edge at its anterior end or a reverse bias blade. An optional further step comprises the determination of the thickness and/or coloration of the walls of the cavity by means of the sonographic equipment, in order to check the walls for malignant conditions. As is well known to those skilled in the operation of sonographic equipment or in the interpretation of sonographic data, coloration may in some instances be determined by variations in echogenicity in a tissue wall. Sonographic examinations in accordance with the invention may be facilitated by the infusion of intraluminal fluid into the cavity to facilitate sonographic examination of cavity, particularly via the catheter and via specially adapted catheters according to the invention. The infusion of such fluids improves transmission of sonographic waves and, especially where fluid-tight seals may be maintained, permits dilation or "inflation" of the cavity so that the cavity structure is more fully extended and more complete examination of the tissue behind its walls is possible. In many instances the procedure is further eased by opening the outer chamber with a speculum and holding it open while the catheter and transducer are emplaced.

It may be seen from the foregoing that the use of the apparatus discussed, and in particular the apparatus aspects of the invention, including the catheter and the biopsy device, contributes directly to the achievement of the objective of the method aspects of the invention.

BRIEF DESCRIPTION OF THE DRAWINGS

FIG. 1a is a cutaway schematic view of a preferred embodiment of an examination, excision, and biopsy device according to the invention. FIG. 1b is a cutaway partial schematic view of a preferred embodiment of an examination, excision, and biopsy device according to the invention, taken from Detail "b" of FIG. 1a.

FIG. 3 is a partial schematic detail of a preferred biopsy device according to the invention.

FIGS. 4a and 4b are a partial schematic details of a preferred biopsy or polypectomy device according to the invention.

FIG. 5 is a partial schematic detail of a preferred biopsy device according to the invention.

FIG. 10a is a schematic top view of an alternative preferred embodiment of an examination, excision, and biopsy device according to the invention. FIG. 10b is a schematic side view of the alternative preferred embodiment of an examination, excision, and biopsy device according to the invention shown in FIG. 10a.

BEST MODE OF CARRYING OUT THE INVENTION

Figure 2:
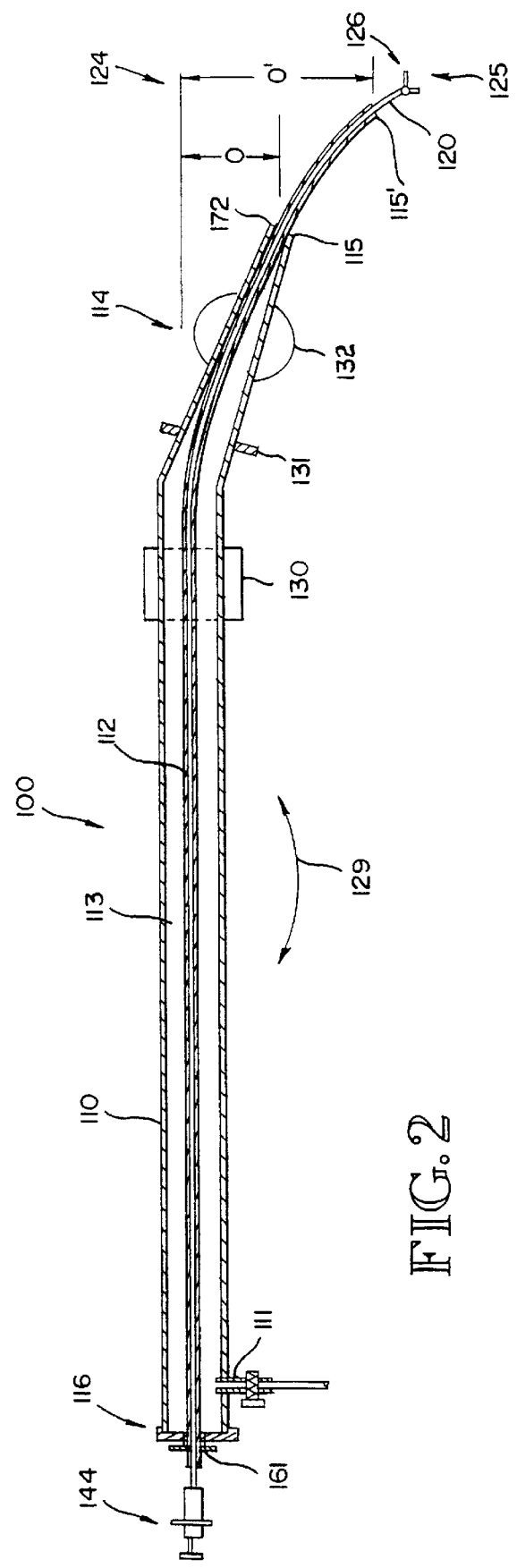
FIG. 2 is a cutaway schematic view of an alternative preferred embodiment of an examination, excision, and biopsy device according to the invention.

As used in this specification, body means any human or animal body, organ, or cadaver, or any part or portion thereof. Tissue includes without limitation flesh, healthy or otherwise, bone, or any other part of a body, or of any body cavity, and any biopsy sample, and any part or portion of any polyps, lesion, malignancy or growth on, within, or originating from a body.

Sonographic examination means any examination or investigation by means of directed sound energy or induced relative displacement of particles or tissues about mean positions, regardless of frequency, and includes ultrasonic examination. Sonographic transducer means any transducer adapted for the transmission and/or reception of sonographic energy, waves, or return, or for the interpretation or mapping thereof.

Intraluminal fluid means any fluid used or intended or adapted for use within the lumen of any cavity or upon any body tissue or structure, and includes fluids used or intended or adapted for use, or suitable for use, in facilitating sonographic examination. Such fluids include, without limitation, saline, lidocaine, betadine, antibiotic solutions, and contrast materials known in the sonographic arts.

Catheter means any substantially tubular instrument suitable for the uses described herein, and includes catheters, sheaths, tubes, and like structures. To say that a catheter or other instrument according to the invention is substantially tubular means that the instrument is generally in the form of an elongated hollow cylinder, which may be of circular or other, more arbitrary cross section.

Turning now to the drawings, the invention will be described in one or more preferred embodiments by reference to the numerals of the drawing figures wherein like numbers indicate like parts.

FIG. 1a is a cutaway schematic view of a preferred embodiment of an examination, excision, and biopsy device according to the invention. Examination, excision, and biopsy device 100 comprises substantially tubular catheter 110 and biopsy device 120. Catheter 110 comprises substantially tubular body 117, interior 113, anterior end 114, tip 115, posterior end 116, and fluid infusion port 111. Interior 113 of the catheter is adapted for the accommodation of a biopsy device such as biopsy device 120 and for the passage of an intraluminal fluid admitted via the fluid infusion port. Catheter 110 is adapted to be substantially fluid tight at all points except optionally at tip 115 (and port 111), so that an intraluminal fluid introduced via, for example, hose 118 or a syringe adapted for attachment to infusion port 111, which may take the form of any conventional valve or flow control device such as a screw-stop valve, may flow through interior 113 (which is in this capacity also sometimes referred to as an irrigation channel), out from tip 115, and into the cavity to be examined so as to facilitate the transmission and reception of sonographic waves. Posterior cap 119 and seal 161, which may be of any conventional form and which may include any conventional valve or sealing means, help maintain fluid tight integrity in the catheter while accommodating passage and retention of biopsy device 120. Catheter 110 further preferably comprises one or more fenders adapted to support the catheter in selected juxtaposition relative to a body cavity in which the catheter has been inserted. For example, the catheter shown in FIG. 1a comprises bumper 131' in the form of an "acorn" bumper. Bumper 131' is shaped so as to engage a wall of the cavity, and preferably a wall between communicating inner and outer chambers of a cavity, so as to restrain the catheter from insertion beyond a desired depth within the cavity (see for example bumper 130 in FIG. 6). Bumper 132 is also adapted to optionally seal a communicating passage in such a wall, so as to create a fluid-tight seal and help retain fluids, such as intraluminal fluids, within the inner chamber. The catheter shown in FIG. 1a further comprises balloon 132, which is adapted for inflation by conventional means after the catheter has been emplaced within the cavity, and typically within the inner chamber or within a passage between inner and outer chambers, so as to keep anterior end 114 of the catheter in a desired position within the cavity, and in particular to prevent undesired contact between the catheter and a wall of the cavity. The shape of balloon 132 may be adapted to position anterior end 114 of the catheter in any number of predetermined or desired positions within the cavity—for example, within the center of the cavity, or off to one side to a greater or lesser extent. Shaping of the balloon will not trouble the skilled designer of such systems. Balloon 132 further optionally provides a seal within the cavity, as described above for the acorn bumper, to facilitate fluid retention within the cavity (see balloon 132 in FIG. 6).

Biopsy device 120 comprises excision device 125, depicted as reverse-bias blade 154, and an optional aspiration means comprising plunger 141, piston 142, and aspiration chamber 143 in the substantially tubular interior of the biopsy device. Biopsy device 120 is in place within the interior of catheter 110, having been inserted tip-first through posterior end 116 (and posterior cap 119) of the catheter through fluid-tight sealing means 161, which as depicted comprises cap screw 162 and o-ring 163, into interior 113 of the catheter, and out of anterior end 114 via tip 115 with excision device 125 protruding from the tip. Biopsy device 120 is restrained, e.g. by tip 115, from radial, or sidewise, movement within the catheter, and, as described, the anterior end of the catheter-biopsy device junction is fluid tight, but the biopsy device is preferably free to move in and out axially within the catheter, so that the extent to which tip 126 of the biopsy device protrudes from tip 115 of the catheter is selectably extendable or retractable. The optional aspiration means permits removal of a collected tissue sample by simple fluid pressure manipulation through operation of plunger 141 and piston 142, as will be readily appreciated by those familiar with aspiration devices, syringes, and the like. For example, a tissue sample collected through engagement of blade 154 with a malignancy on a cavity wall and deposited in cusp 155 of the blade may be drawn up into aspiration chamber 143 by pulling plunger 141 and therefore piston 142 further out of chamber 143, as a result of correspondingly reduced fluid pressure within the chamber. Thereafter the sample may be removed from the cavity without disturbing catheter 110 by simply withdrawing biopsy device 120 from the catheter (after releasing sealing means 161, if necessary). Any suitable aspiration device may be used, as will occur to those skilled in the art of designing biopsy or aspiration devices.

Biopsy device 120 may be provided with any of a wide variety of excision devices for the engagement and collection of tissue samples from the examined cavity. Suitable devices include forceps, snares, baskets, blades, graspers, suction aspiration devices, and cauterization devices. A forceps suitable for use with biopsy devices according to the invention is shown in FIG. 3. Forceps 151 comprises two pincers 156 biased to an open position and closeable by operation of biopsy wire 121 in the direction of arrow 122. Release of the biopsy wire allows the wire to return to its initial position by moving in the direction opposite arrow 122, and allows pincers 126 to close. A snare suitable for use with biopsy devices according to the invention is shown in FIGS. 4a and 4b. Snare 152 is formed by a loop attached to (or integrally part of) biopsy wire 121. With wire 121 appropriately disposed inside needle sheath 123, snare 152 protrudes from the sheath such that it may be looped over tissue 19, which may be a polyps or other similar pendant tissue structure, whereupon by pulling wire 121 in the direction of arrow 122 snare 152 is drawn to a selectable extent into sheath 123, cutting or pulling tissue 19 away from cavity wall 18, so that the tissue may be removed for further examination, disposal, etc. An excision basket suitable for use with biopsy devices according to the invention is shown in FIG. 5. Basket 153 comprises a plurality of blades or wires 157 attached to biopsy wire 121 and collects samples by brushing against and cutting or pulling away abnormality 19', or a portion of it, whereupon the sample may be removed by merely clinging to and being pulled away by the blades or via aspiration through sheath 123 or catheter 110 (not shown).

An example of an excision device particularly well suited for use with the invention is the reverse bias blade previously described. Such blades may be provided either on the catheter or on the biopsy device, or upon a secondary catheter, or sheath, described elsewhere herein. Generally the reverse-bias biopsy blade aspect of the invention comprises a blade disposed at or near the inner or anterior tip of the device of which it is part, as shown in FIGS. 1a and 1b, and adapted to engage tissue on a wall of the cavity when drawn back toward the examination and excision apparatus (generally in the direction 122' shown in FIG. 1b) but generally not when pushed deeper into the cavity (in the sense opposite arrow 122'). By being dragged across or pulled against tissue the blade (blade 154 in FIG. 1b) is enabled to cut the tissue, some portion of which will then be collected in a cusp (such as cusp 155 in FIG. 1b) or equivalent structure, after which collection, as herein elsewhere described, the sample may be removed, either by aspiration, withdrawal of the catheter or biopsy device from the cavity, or other suitable means. A particular advantage of the reverse-bias arrangement is that the blade is prevented from unintended cutting or removal of tissue as the device of which it is part is inserted into the cavity, and cuts or engages tissue only when deliberately placed against a particular tissue structure and dragged or scraped along its surface. Moreover, by the provision of a lip such as lip 159 in FIG. 1b in a location generally in line with the blade, and at a selected offset, the depth of cut or scraping, and the extent of tissue removal may be carefully controlled, so that too deep a cut or removal is not made. The selection of appropriate blade-lip offsets and geometry, and cusp sizing, will not trouble the designer of biopsy devices once he or she has been armed with the disclosure of the invention.

In many instances it is advantageous to provide the examination, biopsy, and excision apparatus of the invention with an optional second catheter, or sheath, inside the primary catheter and outside (or in lieu of) the biopsy or excision device, which is preferably disposed inside the sheath. A configuration embodying such a sheath is shown in FIG. 2. Examination, biopsy, and excision device 100 comprises (primary) catheter 110; inner or secondary catheter, or sheath, 112; and biopsy device 120. Catheter 110 and biopsy device 120 are disposed and sealed as in FIG. 1a, except that sheath 112 is in place around biopsy device 120. One of the advantages offered by utilization of a sheath 112 is that the location of excision device 125 may be more precisely controlled during examination and biopsy procedures. One way in which this is accomplished is to provide the sheath (and/or (primary) catheter 110) with an offset tip, as shown in the Figure. For example, in the apparatus shown in the Figure tip 115 of catheter 110 is offset from centerline 124 of the apparatus (which is generally coaxial with the centerlines of catheter 110, sheath 112, and biopsy device 120) by a distance O, while tip 115' of the sheath is offset by a distance O'. By providing such offset(s) excision device 125 may be given any desired offset from the centerline through simple rotation of the entire apparatus about centerline 124 and/or rotation of sheath 112 within catheter 110. Thus samples may be taken from the further reaches of curved tissue structures or at reaches of the cavity not suitably reached by manipulation of apparatus 100 within the cavity (as for example by rotating apparatus 100 in the direction of arrows 129). Also shown in FIG. 2 is actuator 144, which permits operation of forceps 151 in the conventional manner of many commercially-available biopsy devices.

In general, the examination, excision, and biopsy apparatus of the invention also comprises a sonographic transducer suitable for placement within the outer chamber of a multi-chambered cavity, or within a simple externally communicating cavity, for sonographic examination of the interior. Such transducers may be ultrasonic in nature or may employ methods and transmission of any type suitable for use in conjunction with the apparatus previously described for the purposes given herein. Many such transducers are available commercially, including devices from ATL of Bothell, Washington, and Seimens Corporation of Redmond, Washington.

Figure 6:
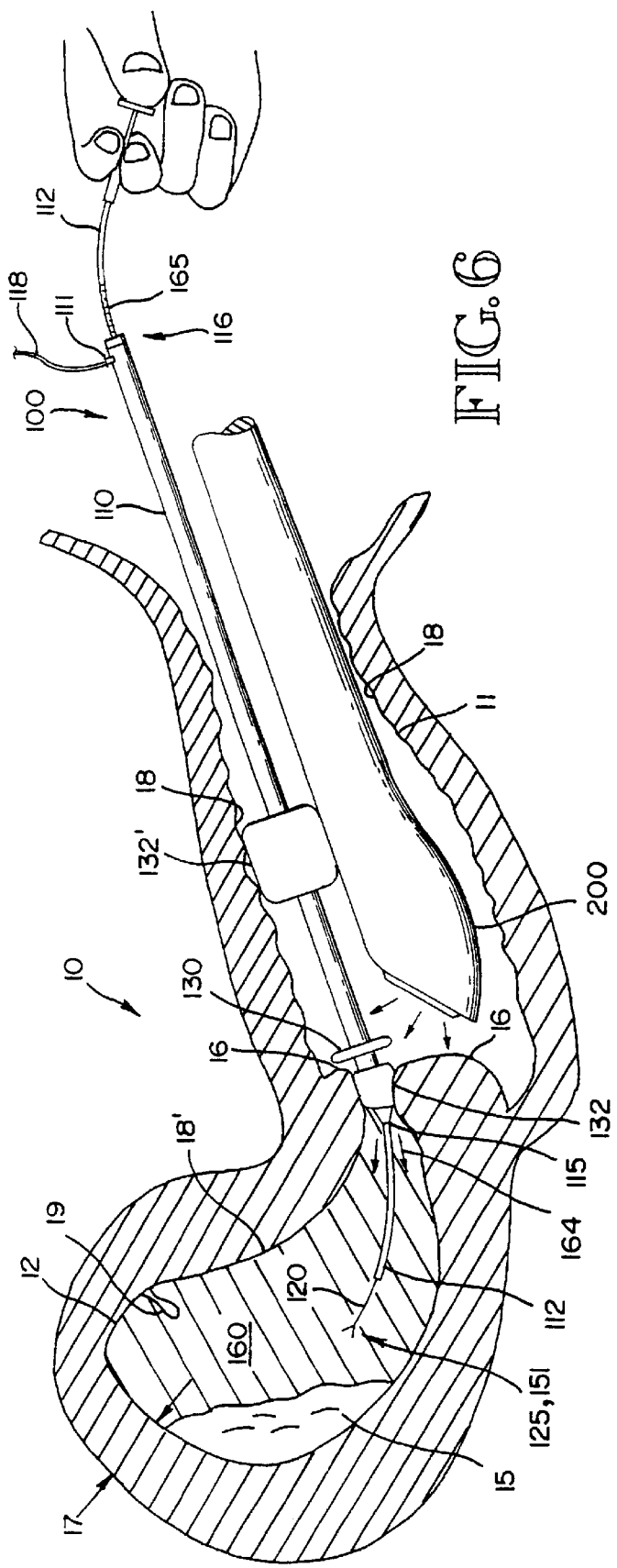
FIG. 6 is a schematic view of preferred embodiments of the aspect and method aspects of the invention in use in a multi-chambered body cavity.

One manner of practicing the method aspect of the invention is depicted in FIG. 6. Sonographic examination, biopsy, and excision apparatus 100 comprises catheter 110, sheath 112, biopsy device 120, and sonographic transducer 200. Catheter 110 and transducer 200 have been placed in outer chamber 11 of externally-communicating multi-chambered cavity 10, which has optionally been previously opened by means of a speculum, with sheath 112 and biopsy device 120 in place inside catheter 110. Catheter 110 has been placed so that bumper 130 is substantially in contact with wall 16 between the outer chamber and inner chamber 12 and is thereby restrained from entering any further. Balloons 132 and 132' have been inflated to hold catheter 110 in place relative to the transducer and the cavity; balloon 132 performs the further function of providing a substantially fluid-tight seal between the inner and outer chambers. Intraluminal fluid 160 has been introduced to inner chamber 12 by infusion through hose 188 (or, for example, a syringe), port 111, and catheter 110, flowing into the inner chamber from tip 115 of the catheter in the direction of arrows 164 to facilitate sonographic transmission within the cavity and to fill and dilate or inflate the chamber to facilitate effective examination. Transducer 200 may then be placed proximate cavity wall 16, with or without use of intraluminal fluid in the outer chamber, so as to permit sonographic examination of inner chamber 12, upon which abnormality 15 may be located and examined, and excision device 125 may be guided to the abnormality to recover a sample of tissue therefrom. When a sample of tissue from the abnormality has been collected by biopsy device 120, it may either be removed from the cavity for further examination by aspiration or by removal of the biopsy device from the catheter by withdrawing it, with or without sheath 112, from catheter 110 via posterior end 116. As will be appreciated, removal of the biopsy device without removing or disturbing catheter 110 allows repeated sampling, or exchanges of biopsy devices or sheaths (which may, for example, be provided with different tip curvatures), while leaving catheter 110 and transducer 200 in place, thus providing substantial potential time savings and accuracy in performing examination and biopsy/excision procedures. While tissue samples are being recovered, thickness 17 of cavity wall 18' or of a membrane such as the endometrium is determined by otherwise conventional sonographic techniques, and wall 18' may be examined for color variations or other conditions known to indicate abnormal or undesirable conditions within the tissue, by for example, variations in echo genicity. In addition, any polyps 19 or other undesirable tissue may be removed by, for example, withdrawing biopsy device 120 from sheath 112 and replacing it with a biopsy device comprising a snare, as previously described, rotating apparatus 100 and sheath 112 such that the snare may be guided to the polyps, and manipulating biopsy device 120 and/or sheath 112 by variously withdrawing or re-inserting them through catheter 110 until the snare is in place around the polyps.

An additional optional and particularly advantageous step involves the use of markings on sheaths and biopsy devices, whereby the relative positions of the tips thereof and of excision devices relative to the tip 115 of the catheter, and tip 115' of the sheath, may be monitored. For example, placing a mark or graduated scale 165 on an external surface of the sheath (as shown in FIG. 6), or on the biopsy device, or both, allows the insertion depth of the biopsy or excision device to be gauged with confidence, so that the insertion depth may be precisely controlled.

It should be noted that the order in which the steps of the procedure are outlined above is generally of little and sometimes no significance. For example, it does not matter whether sheath 112 and/or biopsy device 120 are in place inside catheter 110 when the catheter is placed in the cavity or are inserted thereafter. Indeed, as previously indicated, such sheaths and biopsy devices may be freely interchanged during the procedure, without disturbing the catheter or sonographic transducer and their positioning within the cavity. The important point is that the catheter and sheath act as conduits between the interior of the cavity and the exterior. Nor, for example, does it matter whether the transducer is inserted before, after, or with the catheter. The order of insertion will depend upon many factors, including the type of equipment used, the nature and geometry of the cavity to be examined, and the preference of the practitioner conduction the examination; the selection of a proper order will be well within the ability of a practitioner familiar with examinations and biopsies within body cavities.

When conducted in the manner described, an entire sonographic examination, biopsy, and excision procedure according to the invention may be conducted in as little as 5–10 minutes, with extremely low risk to the patient and at greatly reduced cost when compared with current standard procedures. Moreover, a complete examination and biopsy may be accomplished within a single out-patient level office visit, without overnight or extended hospital stays.

Figure 7:
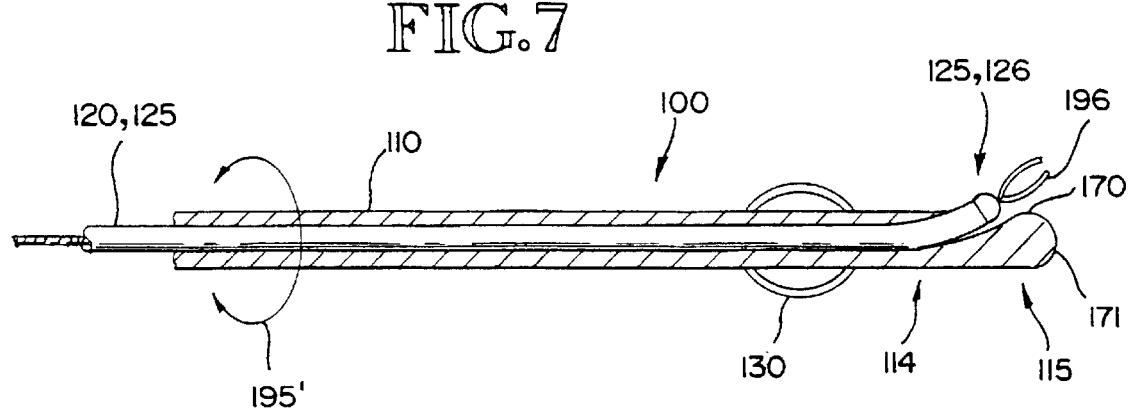
FIG. 7 is a cutaway schematic view of an alternative preferred embodiment of an examination, excision, and biopsy device according to the invention.
Figure 8:
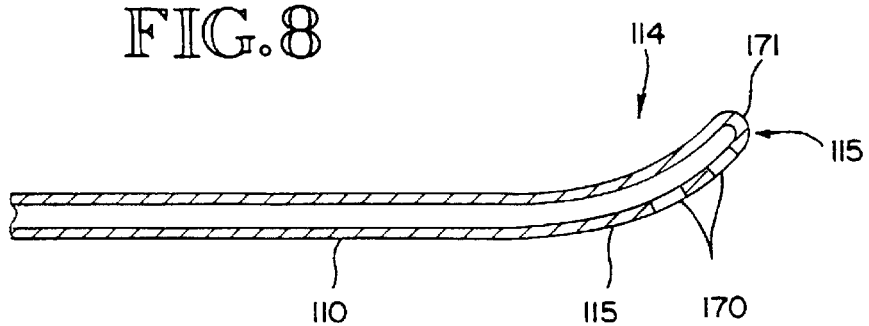
FIG. 8 is a cutaway schematic view of an alternative preferred embodiment of an examination, excision, and biopsy device according to the invention.
Figure 9:
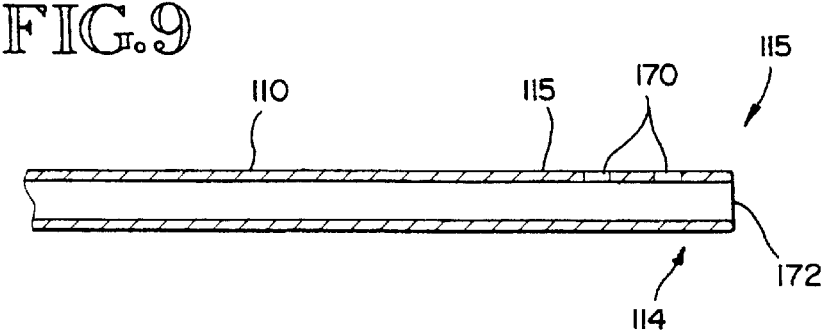
FIG. 9 is a cutaway schematic view of an alternative preferred embodiment of an examination, excision, and biopsy device according to the invention.

FIG. 7 depicts an alternative preferred embodiment of an examination, excision, and biopsy device according to the invention. Anterior end 114 of catheter 110 comprises side port 170 for biopsy or excision device 125. The use of side ports 170 has been found to be extremely advantageous in some circumstances, especially in those requiring relatively precise control in small areas, such as uterine examination and biopsy. By turning examination and biopsy device 100 about its lengthwise axis, in the direction of arrows 195, end 196 of excision or biopsy device 125 can be maneuvered into a wide variety of positions relative to catheter 110. Side ports 170 may also optionally be used for aspiration of tissue or fluid samples. The use of side ports 170 in such fashion has been found to be facilitated in some instances by the use of more than one side port, and by the optional use of curved or offset tips or anterior ends 114 or 115, as shown in FIGS. 8 and 9. Ports 170 are used for aspiration in such instances by placing that portion of catheter 110 comprising the ports proximate or in contact with the tissue wall or other region from which it is desired to remove samples and by applying a negative pressure or partial vacuum inside the catheter, to induce suction at the ports and facilitate entry and subsequent removal of sample material.

Yet another alternative preferred embodiment of an examination, excision, and biopsy device according to the invention is shown in FIGS. 10a and 10b. Catheter 110 comprises length 180, diameter 183, and offset tip 115, which is offset from longitudinal axis 187 of catheter 110 by means of curved anterior end 114, which comprises radius of curvature 181. Anterior end 114 comprises, near tip 115, at least one reverse-bias blade 188. Reverse bias blades 188 are disposed on the sides of anterior end 114 so as to facilitate recovery and removal of tissue samples during biopsy. Optional access port 190 for biopsy, excision, or aspiration devices is also included.

Catheters according to the invention may be provided with either closed or open ends, to facilitate passage of biopsy or excision devices or aspiration of tissue or fluid samples. For example, catheters 110 of FIGS. 7 and 8 comprise closed ends 171, while catheter 110 of FIG. 9 comprises open end 172. Likewise anterior ends 114 or tips 115 of catheters 110 according to the invention may either be straight, as shown in FIGS. 7 and 9, or curved, or offset, as shown in FIGS. 8 and 10a and 10b.

It is also found to be advantageous in many applications to provide both rigid and flexible catheters for use with the invention. Both rigid and flexible catheters are found to be useful in various manipulations. For example, a flexible or at least partially flexible catheter may be useful in reaching various portions of a relatively small chamber such as a uterus with clamps or forceps, while the rigidity of a non-flexible catheter is often useful in recovering material samples through the use of reverse-bias blades, which may require substantial purchase in order to engage and remove tissue samples.

The apparatus components may be made from any suitable materials, including prominently those already known in the art. In general, the catheters, sheaths, and biopsy needles of the invention are made from plastics or other polymers, glass, and various metals, either flexible or substantially rigid, or from combinations thereof. Some or all of the components, and in particular biopsy and excision devices, may be coated to great advantage with echogenic materials or other materials adapted to increase the visibility of the devices by means of sonographic monitors and equipment. The selection of appropriate materials will not be difficult for the designer of such systems, once he or she has been armed with this disclosure.

Sizes and dimensions of the various components of the apparatus aspect of the invention will vary depending upon the types of examination, etc, for which the components will be used. For example, in an apparatus according to the invention intended for use in vaginal/uterine examination as described herein, the (primary) catheter may advantageously be provided with a length of approximately 20 centimeters, and preferably at least 18 centimeters. In some instances, catheters up to 35 or 36 centimeters in length have been used to great advantage for vaginal/uterine examinations. The outer diameter of catheters used in vaginal/uterine examination has most advantageously been selected at between about 5 to about 12 french (about 3 to 4 millimeters); the inner diameter is preferably sufficient to accommodate a 3 to 7 french biopsy device while permitting free infusion of any desired intraluminal fluids. An example of a cervical access catheter satisfactory for use with the invention is the cervical access catheter adapted for use by the addition of a fluid infusion port, a tapered, offset tip, and a posterior seal according to the invention. The selection of suitable lengths for catheters and other instruments for practicing the invention will be well within the ability of practitioners familiar with examination and biopsy in cavities, once they have been given the benefit of this disclosure. For example, as will readily occur to such practitioners, the length of a catheter used for vaginal/uterine examination may advantageously be shortened for women having tight cervices, and to accommodate the use of other or larger instruments, such as bronchoscopy grippers. Conversely, the selection of a relatively long catheter will allow removal of any speculum used for initial opening of the vagina or other cavity. Preferred catheters for vaginal/uterine examination comprise tapered tips for easy insertion in the cervix.

For vaginal/uterine examinations optional inner catheters or sheaths of about 3 to 10 french (1 to 3–⅓ millimeters), and preferably 5 to 7 french, have proven satisfactory. Preferably, inner catheters or sheaths, when used, are about 10 centimeters (and preferably at least 5 centimeters) longer than the outer or primary catheter, and have curved or offset tips. An example of an inner catheter or sheath satisfactory for use with the invention is the fallopian cannulation catheter available from Ackrad Laboratories of Cranford, N.J. Preferred sheaths are marked or graduated in accordance with the disclosure herein, to allow selective protrusion of the tip of the sheath from the outer catheter. Such sheaths are also preferably substantially fluid tight, to prevent back flow or leakage of intraluminal fluid from the cavity.

For vaginal/uterine examinations preferred biopsy devices for use with the invention are 3 to 5 french in diameter and about 10 to 15 centimeters longer than the (primary) catheter. Lengths of about 30 to about 35, or even up to 40 or more, centimeters are preferred. A wide variety of biopsy devices suitable for use with the invention are available, once their length has been adjusted accordingly.

A preferred intraluminal fluid for use with the invention is normal saline. Normal saline is widely available from a number of sources, and is easily prepared by the practitioner when necessary. As previously mentioned, a wide variety of fluids will serve, including lidocaine, betadine, antibiotic solutions, and contrast materials known in the sonographic arts.

With regard to systems and components above referred to, but not otherwise specified or described in detail herein, the workings and specifications of such systems and components and the manner in which they may be made or assembled or used, both cooperatively with each other and with the other elements of the invention described herein to effect the purposes herein disclosed, are all believed to be well within the knowledge of those skilled in the art. No concerted attempt to repeat here what is generally known to the artisan has therefore been made.

As will appear to those making use of the devices and procedures described herein, the use of the apparatus and any compositions of matter discussed herein contributes directly to the achievement of the objective of the methods claimed below.

EXAMPLE

An apparatus for use in combination with a sonographic or fluoroscopic transducer for the examination of and performance of biopsies within an externally communicating multi-chambered body cavities according to the invention, particularly adapted to uterine or endometrial examination, comprises a catheter as shown functionally in FIGS. 10a and 10b and having a length 180 of between 35 and 40 centimeters, and a diameter of 7 or 9 french. The catheter is adapted to receive a biopsy or excision device of 3–7 french diameter. The anterior end of the catheter is curved, the curve having a radius of between about 2 and about 4 centimeters and the curved portion of the catheter having a circumferential length of about 1 to about 2 centimeters, resulting in about a 40° angular offset of the tip from the longitudinal axis of the catheter. The anterior end of the catheter further comprises an ellipsoidal balloon for aid in positioning the catheter inside the body and to prevent injury or discomfort to the patient. The sides of the anterior end also include, at a position about one-half to about one and one-half centimeters from the tip, a pair of reverse bias blades and side ports for the removal and aspiration of tissue samples. Tip 115 of the catheter further comprises opening 172 for passage of an excision or biopsy device as herein described, and for removal of such a device with a tissue sample. Opening 172 also serves, with side ports 170, to permit infusion of intraluminal fluid into the body cavity via port or valve 111.

INDUSTRIAL APPLICABILITY

The invention has applicability to medical procedures and health maintenance. Specifically, the invention provides improvements in sonographic examination, biopsy, and excision within externally communicating cavities of human and other bodies.

In compliance with the statute, the invention has been described in language more or less specific as to structural features. It is to be understood, however, that the invention is not limited to the specific features shown, since the means and construction shown comprise preferred forms of putting the invention into effect. The invention is, therefore, claimed in any of its forms or modifications within the legitimate and valid scope of the appended claims, appropriately interpreted in accordance with the doctrine of equivalents.

I claim:

1. An apparatus for use in combination with a sonographic transducer for examination and performance of biopsies within a uterine chamber and a vaginal chamber of a human female and other bodies, the apparatus comprising:
    (a) a substantially rigid tubular catheter having an anterior end, a posterior end, an exterior surface, and an interior lumen;
    (b) the external surface that is viewable by commonly known ultrasonic and radiographic imaging techniques, such that the catheter is adaptable for use in combination with sonographic examination of uterine and endometrial abnormalities;
    (c) a substantially tapered tip that is offset from the central axis of the catheter located at the anterior end of the catheter;
    (d) a distal port continuous with said internal lumen at said tapered tip;
    (e) at least one bumper affixed to the anterior end of the catheter proximal to said tip, such that the catheter is insertable at least as far as the vaginal chamber, whereby the depth of catheter insertion is limited by a body cavity passage such as the cervix;
    (f) at least one fender located along the external surface of the catheter, proximal to said bumper, whereby the catheter is supportable in a selected juxtaposition relative to the uterine chamber;
    (g) a biopsy device coaxially disposed within the catheter and slidably engaging the internal lumen of the catheter, said biopsy device being longitudinally and rotationally positionable within said catheter, whereby said biopsy device is inserted into the uterine chamber through the catheter, and operationally manipulated while disposed therein; and
    (h) a port at the posterior end of the catheter, whereby said biopsy device is removable (with or without a biopsy sample) and replaceable by an alternate biopsy device while the catheter remains in a fixed operational position within a body cavity.

2. The apparatus of claim 1, whereby said catheter is comprised of at least two coaxially-disposed catheters (one catheter being located inside another), with the biopsy device being disposed within an inner catheter.

3. The inner catheter of claim 2, further comprising a flexible, and substantially tubular body having an anterior end and a posterior end, the anterior end of said inner catheter is curved, whereby the biopsy device is extensively positionable within said uterine chamber.

4. The apparatus of claim 2, further comprising an inflatable balloon adapted to prevent contact between a side of the catheter and a wall of the uterine chamber, such that, when inflated, the balloon prevents accidental removal of the catheter from the uterine chamber, and provides a fluid-tight seal withing the inner chamber.

5. The apparatus of claim 1, whereby the fender is comprised of an inflatable balloon.

6. The apparatus of claim 1, wherein the tip of said catheter is curved.

7. The apparatus of claim 1, further comprising a semi-rigid and flexible tip. whereby said tip provides extensive directional movement while inhibiting inoperable deformation during use.

8. The apparatus of claim 1, wherein said catheter posterior and anterior tip ports, and internal lumen receive a biopsy or excision device that has a diameter between 3 and 7 french (1.00 millimeter and 2.33 millimeters respectively).

9. The apparatus of claim 1, further comprising a sealable posterior port providing a fluid-tight passage for introduction, operation, and removal of a biopsy device therein.

10. The apparatus of claim 1, wherein said catheter is comprised of a plurality of fenders providing a means to support the catheter, whereby the catheter is supportable in a selected juxtaposition relative to the uterine chamber.

11. The apparatus of claim 10, wherein said fenders are comprised of at least one bumper, whereby the catheter is supportable against a wall of the vaginal chamber, thereby restraining the catheter from insertion beyond a desired depth within the uterine chamber.

12. The apparatus of claim 1, wherein the biopsy device is further comprised of a blade, whereby said blade is engageable with tissue within the uterine chamber, and is retractable during deployment and withdrawal of the tissue.

13. The apparatus of claim 1, further comprising at least one secondary lumen for aspirating the tissue from the uterine chamber.

14. The apparatus of claim 1, wherein the biopsy device comprises an excision device adapted for the removal of tissue from the uterine chamber and selected from the group comprising forceps, snares, baskets, cauterizing devices, suction aspiration catheters, reverse bias blades, and brushes.

15. The apparatus of claim 1, wherein the anterior end of said catheter comprises at least one side port.

16. A method for the sonographic examination of a multi-chambered body cavity comprising a uterine chamber, and a vaginal chamber communicating with the uterine chamber, and for the removal of tissue from the cavity, the method comprising the steps of:

inserting a substantially tubular catheter into the vaginal chamber at least as far as the vaginal chamber;

inserting an excision device into the uterine chamber through the catheter; inserting a sonographic transducer within the vaginal chamber in substantial proximity to the uterine chamber, whereby sonographic examination of the uterine chamber is enabled;

sonographically examining the uterine chamber;

sonographically guiding the excision device to an abnormality within the uterine chamber;

sonographically locating the abnormality within the uterine chamber;

removing a biopsy tissue sample of the abnormality with said excision device; and removing said excision device and tissue sample through the catheter, whereby the catheter and sonographic transducer remain in their inserted positions for continued operation.

17. The method of claim 16, further comprising the step of infusing an intraluminal fluid into the cavity to facilitate sonographic examination of the uterine chamber.

18. The method of claim 17, wherein the intra luminal fluid is introduced to the uterine chamber via the catheter.

19. The method of claim 16, further comprising the step of determining the thickness of a tissue wall by means of sonographic imaging.

20. The method of claim 16, further comprising the step of determining the homogeneity of a tissue wall by means of sonographic imaging.

21. The method of claim 16, wherein the excision device comprises a snare and the method further comprises the step of engaging and removing polyps.

22. The method of claim 16, wherein the excision device is selected from the group consisting of a forceps, basket, and brush.

* * * * *